United States Patent
Hayter et al.

(10) Patent No.: US 12,254,978 B2
(45) Date of Patent: *Mar. 18, 2025

(54) COMPATIBILITY MECHANISMS FOR DEVICES IN A CONTINUOUS ANALYTE MONITORING SYSTEM AND METHODS THEREOF

(71) Applicant: ABBOTT DIABETES CARE INC., Alameda, CA (US)

(72) Inventors: Gary Alan Hayter, Oakland, CA (US); Andrew H. Naegeli, Walnut Creek, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/236,520

(22) Filed: Aug. 22, 2023

(65) Prior Publication Data

US 2024/0038381 A1 Feb. 1, 2024

Related U.S. Application Data

(63) Continuation of application No. 17/523,527, filed on Nov. 10, 2021, now Pat. No. 11,783,941, which is a continuation of application No. 15/640,058, filed on Jun. 30, 2017, now Pat. No. 11,205,511, which is a continuation of application No. 15/065,604, filed on Mar. 9, 2016, now Pat. No. 9,721,063, which is a
(Continued)

(51) Int. Cl.
*G06K 7/10* (2006.01)
*G16B 50/00* (2019.01)
*G16B 50/30* (2019.01)
*G16H 40/63* (2018.01)
*G16H 40/67* (2018.01)

(52) U.S. Cl.
CPC ......... *G16H 40/63* (2018.01); *G06K 7/10009* (2013.01); *G16B 50/00* (2019.02); *G16B 50/30* (2019.02); *G16H 40/67* (2018.01)

(58) Field of Classification Search
CPC ........ G16H 40/63; G16B 50/30; G16B 50/00; G06K 7/10009
USPC ....................................................... 235/380
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

*Ancora Technologies, Inc. v. HTC America, Inc.*, U.S. Court of Appeals for the Federal Circuit, Opinion, Appeal No. 18-1404, Nov. 16, 2018, pp. 1-13.

(Continued)

*Primary Examiner* — Daniel A Hess
(74) *Attorney, Agent, or Firm* — ONE LLP

(57) ABSTRACT

Methods, devices, and kits are provided for determining a compatibility of one or more devices in an analyte monitoring system.

22 Claims, 6 Drawing Sheets

Related U.S. Application Data continuation of application No. 13/684,085, filed on Nov. 21, 2012, now Pat. No. 9,317,656.

(60) Provisional application No. 61/563,517, filed on Nov. 23, 2011.

(56) References Cited

U.S. PATENT DOCUMENTS

| | | |
|---|---|---|
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,759,828 A | 7/1988 | Young et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,640,954 A | 6/1997 | Pfeiffer et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,735,285 A | 4/1998 | Albert et al. |
| 5,748,103 A | 5/1998 | Flach et al. |
| 5,771,891 A | 6/1998 | Gozani |
| 5,772,586 A | 6/1998 | Heinonen et al. |
| 5,791,344 A | 8/1998 | Schulman et al. |
| 5,807,375 A | 9/1998 | Gross et al. |
| 5,875,186 A | 2/1999 | Belanger et al. |
| 5,899,855 A | 5/1999 | Brown |
| 5,914,026 A | 6/1999 | Blubaugh, Jr. et al. |
| 5,925,021 A | 7/1999 | Castellano et al. |
| 5,942,979 A | 8/1999 | Luppino |
| 5,951,521 A | 9/1999 | Mastrototaro et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,315 A | 2/2000 | Iliff |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,134,461 A | 10/2000 | Say et al. |
| 6,141,573 A | 10/2000 | Kurnik et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |

(56) References Cited

U.S. PATENT DOCUMENTS

| | | |
|---|---|---|
| 6,212,416 B1 | 4/2001 | Ward et al. |
| 6,219,574 B1 | 4/2001 | Cormier et al. |
| 6,223,283 B1 | 4/2001 | Chaiken et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,045 B1 | 11/2002 | Holker et al. |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,728,877 B2 | 4/2004 | Mackin et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,024,245 B2 | 4/2006 | Lebel et al. |
| 7,025,774 B2 | 4/2006 | Freeman et al. |
| 7,027,848 B2 | 4/2006 | Robinson et al. |
| 7,027,931 B1 | 4/2006 | Jones et al. |
| 7,041,068 B2 | 5/2006 | Freeman et al. |
| 7,041,468 B2 | 5/2006 | Drucker et al. |
| 7,046,153 B2 | 5/2006 | Oja et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,442 B2 | 6/2007 | Sheppard et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,329,239 B2 | 2/2008 | Safabash et al. |
| 7,346,766 B2 | 3/2008 | Mackin et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |

(56) References Cited

U.S. PATENT DOCUMENTS

| | | |
|---|---|---|
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 | 6/2010 | Taub |
| 7,736,344 B2 | 6/2010 | Moberg et al. |
| 7,763,042 B2 | 7/2010 | Iio et al. |
| 7,766,829 B2 | 8/2010 | Sloan et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,889,069 B2 | 2/2011 | Fifolt et al. |
| 7,899,545 B2 | 3/2011 | John |
| 7,914,460 B2 | 3/2011 | Melker et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,969,307 B2 | 6/2011 | Peeters |
| 7,972,296 B2 | 7/2011 | Braig et al. |
| 7,976,466 B2 | 7/2011 | Ward et al. |
| 7,978,063 B2 | 7/2011 | Baldus et al. |
| 8,010,174 B2 | 8/2011 | Goode, Jr. et al. |
| 8,010,256 B2 | 8/2011 | Oowada |
| 8,192,394 B2 | 6/2012 | Estes et al. |
| 8,255,026 B1 | 8/2012 | Al-Ali |
| 8,282,549 B2 | 10/2012 | Brauker et al. |
| 8,597,570 B2 | 12/2013 | Terashima et al. |
| 9,317,656 B2 * | 4/2016 | Hayter .................. G16B 50/00 |
| 9,721,063 B2 * | 8/2017 | Hayter .................. G16H 40/63 |
| 11,205,511 B2 * | 12/2021 | Hayter .................. G16B 50/00 |
| 11,783,941 B2 * | 10/2023 | Hayter ............... G06K 7/10009 |
| | | 235/380 |
| 2001/0020124 A1 | 9/2001 | Tamada |
| 2001/0037060 A1 | 11/2001 | Thompson et al. |
| 2001/0037366 A1 | 11/2001 | Webb et al. |
| 2001/0047604 A1 | 12/2001 | Valiulis |
| 2002/0019022 A1 | 2/2002 | Dunn et al. |
| 2002/0054320 A1 | 5/2002 | Ogino |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0128594 A1 | 9/2002 | Das et al. |
| 2002/0133107 A1 | 9/2002 | Darcey |
| 2002/0147135 A1 | 10/2002 | Schnell |
| 2002/0161288 A1 | 10/2002 | Shin et al. |
| 2002/0188748 A1 | 12/2002 | Blackwell et al. |
| 2003/0005464 A1 | 1/2003 | Gropper et al. |
| 2003/0021729 A1 | 1/2003 | Moller et al. |
| 2003/0023461 A1 | 1/2003 | Quintanilla et al. |
| 2003/0028089 A1 | 2/2003 | Galley et al. |
| 2003/0060692 A1 | 3/2003 | Ruchti et al. |
| 2003/0060753 A1 | 3/2003 | Starkweather et al. |
| 2003/0114897 A1 | 6/2003 | Von Arx et al. |
| 2003/0147515 A1 | 8/2003 | Kai et al. |
| 2003/0163351 A1 | 8/2003 | Brown |
| 2003/0168338 A1 | 9/2003 | Gao et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2004/0010207 A1 | 1/2004 | Flaherty et al. |
| 2004/0015102 A1 | 1/2004 | Cummings et al. |
| 2004/0041749 A1 | 3/2004 | Dixon |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0073266 A1 | 4/2004 | Haefner et al. |
| 2004/0078215 A1 | 4/2004 | Dahlin et al. |
| 2004/0106858 A1 | 6/2004 | Say et al. |
| 2004/0122353 A1 | 6/2004 | Shahmirian et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0204687 A1 | 10/2004 | Mogensen et al. |
| 2004/0204868 A1 | 10/2004 | Maynard et al. |
| 2004/0223985 A1 | 11/2004 | Dunfiled et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0027177 A1 | 2/2005 | Shin et al. |
| 2005/0031689 A1 | 2/2005 | Shults et al. |
| 2005/0038680 A1 | 2/2005 | McMahon |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0137530 A1 | 6/2005 | Campbell et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0195930 A1 | 9/2005 | Spital et al. |
| 2005/0204134 A1 | 9/2005 | Von Arx et al. |
| 2005/0214892 A1 | 9/2005 | Kovatchev et al. |
| 2005/0245799 A1 | 11/2005 | Brauker et al. |
| 2005/0251033 A1 | 11/2005 | Scarantino et al. |
| 2005/0277912 A1 | 12/2005 | John |
| 2006/0001538 A1 | 1/2006 | Kraft et al. |
| 2006/0001551 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0017923 A1 | 1/2006 | Ruchti et al. |
| 2006/0020300 A1 | 1/2006 | Nghiem et al. |
| 2006/0031094 A1 | 2/2006 | Cohen et al. |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Haves et al. |
| 2006/0189863 A1 | 8/2006 | Peyser et al. |
| 2006/0193375 A1 | 8/2006 | Lee et al. |

(56) References Cited

U.S. PATENT DOCUMENTS

| | | |
|---|---|---|
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0247985 A1 | 11/2006 | Liamos et al. |
| 2006/0258929 A1 | 11/2006 | Goode et al. |
| 2006/0272652 A1 | 12/2006 | Stocker et al. |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0016381 A1 | 1/2007 | Karnath et al. |
| 2007/0017983 A1 | 1/2007 | Frank et al. |
| 2007/0027381 A1 | 2/2007 | Stafford |
| 2007/0033074 A1 | 2/2007 | Nitzan et al. |
| 2007/0060869 A1 | 3/2007 | Tolle et al. |
| 2007/0060979 A1 | 3/2007 | Strother et al. |
| 2007/0066956 A1 | 3/2007 | Finkel |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0149875 A1 | 6/2007 | Ouyang et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0191702 A1 | 8/2007 | Yodfat et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208246 A1 | 9/2007 | Brauker et al. |
| 2007/0228071 A1 | 10/2007 | Kamen et al. |
| 2007/0231846 A1 | 10/2007 | Cosentino et al. |
| 2007/0232878 A1 | 10/2007 | Kovatchev et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0255348 A1 | 11/2007 | Holtzclaw |
| 2008/0004904 A1 | 1/2008 | Tran |
| 2008/0009692 A1 | 1/2008 | Stafford |
| 2008/0033254 A1 | 2/2008 | Karnath et al. |
| 2008/0039702 A1 | 2/2008 | Hayter et al. |
| 2008/0045824 A1 | 2/2008 | Tapsak et al. |
| 2008/0060955 A1 | 3/2008 | Goodnow |
| 2008/0061961 A1 | 3/2008 | John |
| 2008/0083617 A1 | 4/2008 | Simpson et al. |
| 2008/0092638 A1 | 4/2008 | Brenneman et al. |
| 2008/0114228 A1 | 5/2008 | McCluskey et al. |
| 2008/0125636 A1 | 5/2008 | Ward et al. |
| 2008/0127052 A1 | 5/2008 | Rostoker |
| 2008/0177149 A1 | 7/2008 | Weinert et al. |
| 2008/0194934 A1 | 8/2008 | Ray et al. |
| 2008/0194938 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0287764 A1 | 11/2008 | Rasdal et al. |
| 2008/0296155 A1 | 12/2008 | Shults et al. |
| 2008/0300572 A1 | 12/2008 | Rankers et al. |
| 2008/0306434 A1 | 12/2008 | Dobbles et al. |
| 2008/0306435 A1 | 12/2008 | Karnath et al. |
| 2008/0306444 A1 | 12/2008 | Brister et al. |
| 2008/0312859 A1 | 12/2008 | Skyggebjerg et al. |
| 2008/0319085 A1 | 12/2008 | Wright et al. |
| 2009/0006061 A1 | 1/2009 | Thukral et al. |
| 2009/0012377 A1 | 1/2009 | Jennewine et al. |
| 2009/0018424 A1 | 1/2009 | Karnath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0048503 A1 | 2/2009 | Dalal et al. |
| 2009/0054747 A1 | 2/2009 | Fennell |
| 2009/0062633 A1 | 3/2009 | Brauker et al. |
| 2009/0076356 A1 | 3/2009 | Simpson et al. |
| 2009/0076360 A1 | 3/2009 | Brister et al. |
| 2009/0082693 A1 | 3/2009 | Stafford |
| 2009/0085873 A1 | 4/2009 | Betts et al. |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0156924 A1 | 6/2009 | Shariati et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Karnath et al. |
| 2009/0192751 A1 | 7/2009 | Karnath et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Karnath et al. |
| 2009/0242425 A1 | 10/2009 | Karnath et al. |
| 2009/0247855 A1 | 10/2009 | Boock et al. |
| 2009/0247856 A1 | 10/2009 | Boock et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0004521 A1* | 1/2010 | Epps .................... A61B 5/411 600/347 |
| 2010/0076283 A1 | 3/2010 | Simpson et al. |
| 2010/0093786 A1 | 4/2010 | Watanabe et al. |
| 2010/0096259 A1 | 4/2010 | Zhang et al. |
| 2010/0105999 A1 | 4/2010 | Dixon et al. |
| 2010/0113897 A1 | 5/2010 | Brenneman et al. |
| 2010/0141656 A1 | 6/2010 | Krieftewirth |
| 2010/0146300 A1 | 6/2010 | Brown |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168540 A1 | 7/2010 | Karnath et al. |
| 2010/0168541 A1 | 7/2010 | Karnath et al. |
| 2010/0168542 A1 | 7/2010 | Karnath et al. |
| 2010/0168543 A1 | 7/2010 | Karnath et al. |
| 2010/0168544 A1 | 7/2010 | Karnath et al. |
| 2010/0168545 A1 | 7/2010 | Karnath et al. |
| 2010/0168546 A1 | 7/2010 | Karnath et al. |
| 2010/0168657 A1 | 7/2010 | Karnath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |

(56) References Cited

U.S. PATENT DOCUMENTS

| | | |
|---|---|---|
| 2010/0179402 A1 | 7/2010 | Goode, Jr. et al. |
| 2010/0179405 A1 | 7/2010 | Goode, Jr. et al. |
| 2010/0179408 A1 | 7/2010 | Karnath et al. |
| 2010/0179409 A1 | 7/2010 | Karnath et al. |
| 2010/0185065 A1 | 7/2010 | Goode, Jr. et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0198034 A1 | 8/2010 | Thomas et al. |
| 2010/0198035 A1 | 8/2010 | Karnath et al. |
| 2010/0198142 A1 | 8/2010 | Sloan et al. |
| 2010/0213080 A1 | 8/2010 | Celentano et al. |
| 2010/0217105 A1 | 8/2010 | Yodfat et al. |
| 2010/0262201 A1 | 10/2010 | He et al. |
| 2010/0313105 A1 | 12/2010 | Nekoomaram et al. |
| 2010/0331642 A1 | 12/2010 | Bruce et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0112696 A1 | 5/2011 | Yodfat et al. |
| 2011/0148905 A1 | 6/2011 | Simmons et al. |
| 2011/0178461 A1 | 7/2011 | Chong et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0287528 A1 | 11/2011 | Fern et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| EP | 0320109 | 6/1989 |
| EP | 0390390 | 10/1990 |
| EP | 0396788 | 11/1990 |
| WO | WO-00/59370 | 10/2000 |
| WO | WO-01/52935 | 7/2001 |
| WO | WO-01/54753 | 8/2001 |
| WO | WO-03/82091 | 10/2003 |
| WO | WO-2008/001366 | 1/2008 |

OTHER PUBLICATIONS

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.

Bennion, N., et al., "Alternate Site Glucose Testing: A Crossover Design", Diabetes Technology & Therapeutics. vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-line Glucose Sensor for Fermentation Monitoring", Biosensors, vol. 3, 1987, pp. 45-56.

Cass, A. E.G., et al., "Ferrocene-Medicated Enzyme Electrode for Amperometric Determination of Glucose", Analytical Chemistry, vol. 56, No. 4, 1984, pp. 667-671.

Csoregi, E., et al., "Design and Optimization of a Selective Subcutaneously Implantable Glucose Electrode Based on "Wired" Glucose Oxidase", Analytical Chemistry, vol. 67, No. 7, 1995, pp. 1240-1244.

El-Khatib, F. H., et al., "Adaptive Closed-Loop Control Provides Blood-Glucose Regulation Using Subcutaneous Insulin and Glucagon Infusion in Diabetic Swine", Journal of Science and Technology, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5 No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, p. 198.

Jungheim, K., et al., "How Rapid Does Glucose Concentration Change in Daily Life of Patients With Type 1 DIABETES?", Diabetologia, vol. 45, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Lortz, J., et al., "What is Bluetooth? We Explain The Newest Short-Range Connectivity Technology", Smart Computing Learning Series, Wireless Computing, vol. 8, Issue 5, 2002, pp. 72-74.

Malin, S. F., et al., "Noninvasive Prediction of Glucose by Near-Infrared Diffuse Reflectance Spectroscopy", Clinical Chemistry, vol. 45, No. 9, 1999, pp. 1651-1658.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Morbiducci, U., et al., "Improved usability of the minimal model of insulin sensitivity based on an automated approach and genetic algorithms for parameter estimation", Clinical Science, vol. 112, 2007, pp. 257-263.

Mougiakakou, S.G., et al., "A Real Time Simulation Model of Glucose-Insulin Metabolism for Type 1 Diabetes Patients", Proceedings of the 2005 IEEE Engineering in Medicine and Biology 27th Annual Conference, 2005, pp. 298-301.

Parker, R., et al., "Robust H∞ Glucose Control in Diabetes Using a Physiological Model", AIChE Journal, vol. 46, No. 12, 2000, pp. 2537-2549.

Pickup, J. C., et al., "Implantable Glucose Sensors: Choosing the Appropriate Sensing Strategy", Biosensors, vol. 3, 1987/88, pp. 335-346.

Pickup, J. C., et al., "In vivo molecular sensing in diabetes mellitus: an implantable glucose sensor with direct electron transfer", Diabetologia, vol. 32, 1989, pp. 213-217.

Pishko, M. V., et al., "Amperometric Glucose Microelectrodes Prepared through t hrough Immobilization of Glucose Oxidase in Redox Hydrogels", Analytical Chemistry, vol. 63, No. 20, 1991, pp. 2268-2272.

Quinn, C. P., et al., "Kinetics of glucose delivery to subcutaneous tissue in rats measured with 0.3-mm amperometric microsensors", American Journal of Physiology, vol. 269, No. 1, 1995, E155-E161.

(56) References Cited

OTHER PUBLICATIONS

Roe, J. N., et al., "Bloodless Glucose Measurements", Critical Reviews™ in Therapeutic Drug Carrier Systems, vol. 15, Issue 3, 1998, pp. 199-241.
Sakakida, M., et al., "Development of ferrocene-mediated needle-type glucose sensor as a measure of true subcutaneous tissue glucose concentrations", Artificial Organs Today, vol. 2, No. 2, 1992, pp. 145-158.
Sakakida, M., et al., "Ferrocene-mediated needle-type glucose sensor covered with newly designed biocompatible membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and modeling of the transient difference between blood and subcutaneous glucose concentrations in the rat after injection of insulin", Proceedings of the National Academy of Sciences, vol. 95, 1998, pp. 294-299.
Shaw, G. W., et al., "In Vitro testing of a simply constructed, highly s table glucose sensor suitable for implantation in diabetic patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane design for extending the long-life of an implantable glucose sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-type Enzyme-based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A.P.F., et al., "Diabetes Mellitus: Biosensors for Research and Management", Biosensors, vol. 1, 1985, pp. 85-115.
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.
Velho, G., et al., "Strategies for calibrating a subcutaneous glucose sensor", Biomedica Biochimica Acta, vol. 48, 1989, pp. 957-964.
Wilson, G. S., et al., "Progress toward the Development of an Implantable Sensor for Glucose", Clinical Chemistry, vol. 38, No. 9, 1992, pp. 1613-1617.

\* cited by examiner

COMPATIBILITY MECHANISMS FOR DEVICES IN A CONTINUOUS ANALYTE MONITORING SYSTEM AND METHODS THEREOF

RELATED APPLICATIONS

The present application is a continuation of U.S. patent application Ser. No. 17/523,527, filed Nov. 10, 2021, which is a continuation of U.S. patent application Ser. No. 15/640,058, filed Jun. 30, 2017, now U.S. Pat. No. 11,205,511, which is a continuation of U.S. patent application Ser. No. 15/065,604, filed Mar. 9, 2016, now U.S. Pat. No. 9,721,063, which is a continuation of U.S. patent application Ser. No. 13/684,085, filed Nov. 21, 2012, now U.S. Pat. No. 9,317,656, which claims the benefit of U.S. Provisional Patent Application No. 61/563,517, filed Nov. 23, 2011, all of which are incorporated herein by reference in their entireties for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

SUMMARY

Embodiments of the present disclosure include computer-implemented methods for determining a compatibility of one or more devices in an analyte monitoring system. Certain aspects include receiving identification code data related to a configuration of a first device, retrieving information including a predetermined list of one or more acceptable identification code data that is related to one or more first device configurations that are compatible with the analyte monitoring system, comparing the received identification code data with the one or more acceptable identification codes from the retrieved predetermined list and determining if the configuration of the first device is compatible with the analyte monitoring system based upon the received identification code data being identified in the predetermined list of acceptable identification code data.

Embodiments of the present disclosure include computer-implemented methods for determining a compatibility of one or more devices in an analyte monitoring system. Certain aspects include receiving identification code data related to a configuration of a first device, retrieving information including a predetermined list of one or more identification codes that are related to one or more first device configurations and one or more software functions relating to the one or more first device configurations, comparing the received identification code data with the one or more identification codes and determining an appropriate software function for processing analyte data obtained by the first device that is related to an analyte level of a user based upon a stored software function that corresponds to the received identification code data.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although many methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Figure 1:
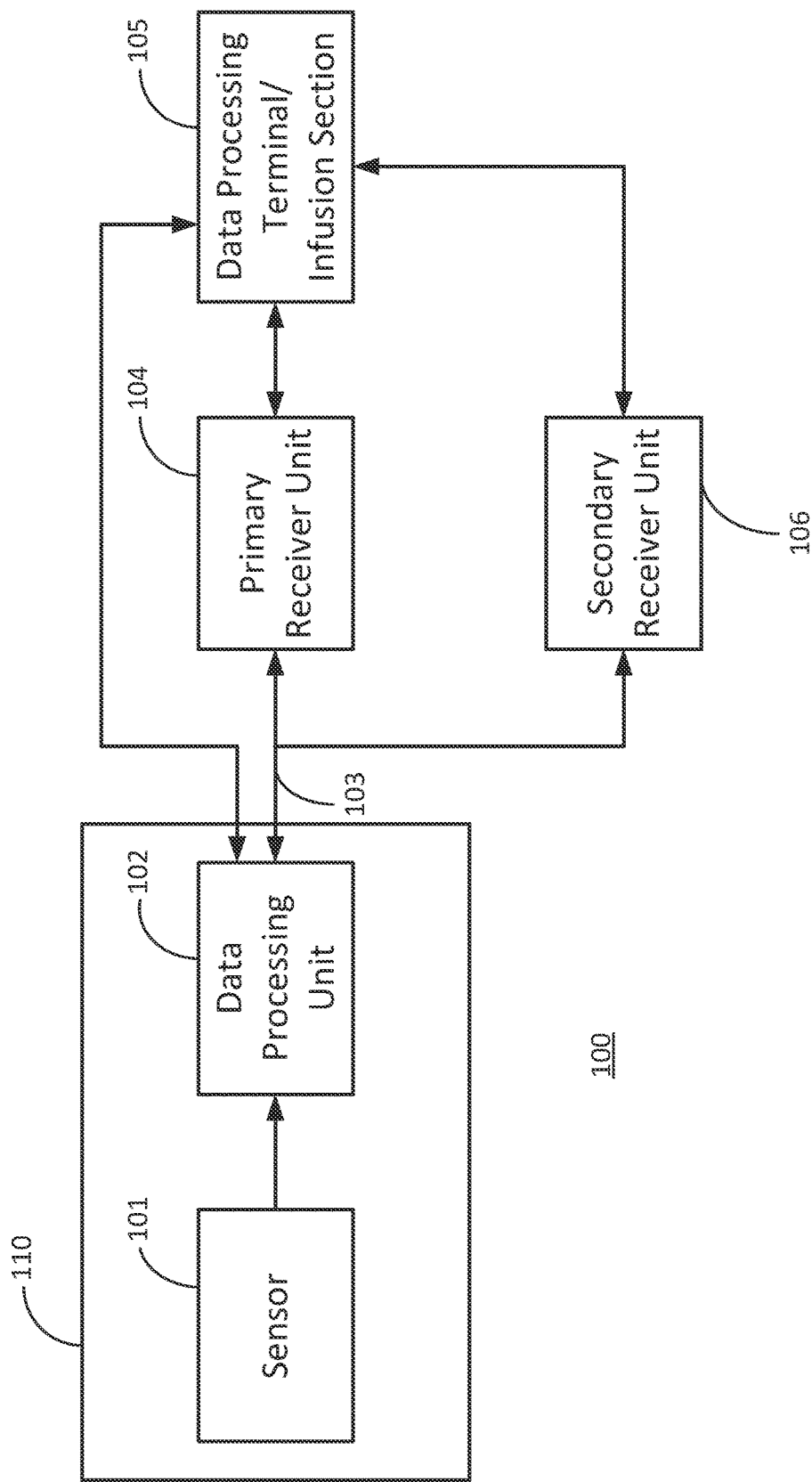
FIG. 1 illustrates a block diagram of a data monitoring and management system for practicing one or more embodiments of the present disclosure.

FIG. 1 shows a data monitoring and management system such as, for example, an analyte (e.g., glucose) monitoring system in accordance with certain embodiments of the present disclosure. Embodiments of the subject disclosure are described primarily with respect to glucose monitoring devices and systems, and methods of using two or more devices in a glucose monitoring system to determine the compatibility of one or more devices in the glucose monitoring system.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

Referring to FIG. 1, the analyte monitoring system 100 includes a sensor 101, a data processing unit (e.g., sensor electronics) 102 connectable to the sensor 101, and a primary receiver unit 104 which is configured to communicate with the data processing unit 102 via a communication link 103. In aspects of the present disclosure, the sensor 101 and the data processing unit (sensor electronics) 102 may be configured as a single integrated assembly 110. In certain embodiments, the integrated sensor and sensor electronics assembly 110 may be configured as an on-body patch device. In such embodiments, the on-body patch device may be configured for, for example, RFID or RF communication with a reader device/receiver unit, and/or an insulin pump.

In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver unit 104, i.e., the secondary receiver unit 106 may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least process and send data related to its configuration into a corresponding signal for transmission by the data processing unit 102.

The data processing unit 102 is coupleable to the sensor 101 so that both devices are positioned in or on the user's body, with at least a portion of the analyte sensor 101 positioned transcutaneously. The data processing unit 102 in certain embodiments may include a portion of the sensor 101 (proximal section of the sensor in electrical communication with the data processing unit 102) which is encapsulated within or on the printed circuit board of the data processing unit 102 with, for example, potting material or other protective material. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, identification information of the data processing unit 102, and thereafter, to periodically receive signals transmitted from the data processing unit 102 associated with the monitored analyte levels detected by the sensor 101. That is, when operating in the CGM mode, the receiver unit 104 in certain embodiments is configured to automatically receive data related to the configuration of the sensor from the analyte sensor/sensor electronics when the communication link (e.g., RF range) is maintained or opened between these components.

Referring again to FIG. 1, the data processing terminal 105 may include a personal computer, portable data processing devices or computers such as a laptop computer or a handheld device (e.g., personal digital assistants (PDAs), communication devices such as a cellular phone (e.g., a multimedia and Internet-enabled mobile phone such as an iPhone, a Blackberry device, a Palm device such as Palm Pre, Treo, or similar phone), mp3 player, pager, and the like), drug delivery device, insulin pump, each of which may be configured for data communication with the receiver via a wired or a wireless connection. Additionally, the data processing terminal 105 may further be connected to a data network (not shown).

The data processing terminal 105 may include an infusion device such as an insulin infusion pump or the like, which may be configured to administer insulin to patients, and which may be configured to communicate with the primary receiver unit 104 for receiving, among others, the measured analyte level or configuration data. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the configuration signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

As described in aspects of the present disclosure, the analyte monitoring system may include an on-body patch device with a thin profile that can be worn on the arm or other locations on the body (and under clothing worn by the user or the patient), the on-body patch device including an analyte sensor and circuitry and components for operating the sensor and processing and storing signals, including configuration signals, received from the sensor as well as for communication with the reader device. For example, one aspect of the on-body patch device may include electronics to sample the voltage signal received from the analyte sensor in fluid contact with the body fluid, and to process the sampled voltage signals into the corresponding glucose values and/or store the sampled voltage signal as raw data, or to send configuration information as a signal or data.

In certain embodiments, the on-body patch device includes an antenna such as a loop antenna to receive RF power from an external device such as the reader device/receiver unit described above, electronics to convert the RF power received via the antenna into DC (direct current) power for the on-body patch device circuitry, communication module or electronics to detect commands received from the reader device, and communication component to transmit data to the reader device, a low capacity battery for providing power to sensor sampling circuitry (for example, the analog front end circuitry of the on-body patch device in signal communication with the analyte sensor), one or more non-volatile memory or storage devices to store data including raw signals from the sensor or processed data based on the raw sensor signals. More specifically, in the on operation demand mode, the on-body patch device in certain embodiments is configured to transmit real time analyte related data and/or stored historical analyte related data, and/or configuration data when within the RF power range of the reader device. The configuration data can be transmitted prior to transmitting the real time analyte related data.

In certain embodiments, a data processing module/terminal may be provided in the analyte monitoring system that is configured to operate as a data logger, interacting or communicating with the on-body patch device by, for example, transmitting requests for configuration information to the on-body patch device, and storing the responsive configuration information received from the on-body patch device in one or more memory components of the data processing module (e.g., repeater unit). Further, data processing module may be configured as a compact on-body relay device to relay or retransmit the received analyte level information from the on-body patch device to the reader device/receiver unit or the remote terminal or both. The data processing module in one aspect may be physically coupled to the on-body patch device, for example, on a single adhesive patch on the skin surface of the patient. Alternatively, the data processing module may be positioned close to but not in contact with the on-body patch device. For example, when the on-body patch device is positioned on the abdomen of the patient, the data processing module may be worn on a belt of the patient or the user, such that the desired close proximity or predetermined distance of approximately 1-5 inches (or about 1-10 inches, for example, or more) between the on-body patch device and the data processing module may be maintained.

The various processes described above including the processes operating in the software application execution environment in the analyte monitoring system including the on-body patch device, the reader device, data processing module and/or the remote terminal performing one or more routines described above may be embodied as computer programs developed using an object oriented language that allows the modeling of complex systems with modular objects to create abstractions that are representative of real world, physical objects and their interrelationships. The software required to carry out the inventive process, which may be stored in a memory or storage device of the storage unit of the various components of the analyte monitoring system described above in conjunction to the Figures including the on-body patch device, the reader device, the data processing module, various described communication devices, or the remote terminal may be developed by a person of ordinary skill in the art and may include one or more computer program products.

In one embodiment, an apparatus for bi-directional communication with an analyte monitoring system may comprise a storage device having stored therein one or more routines, a processing unit operatively coupled to the storage device and configured to retrieve the stored one or more routines for execution, a data transmission component operatively coupled to the processing unit and configured to transmit data based at least in part on the one or more routines executed by the processing unit, and a data reception component operatively coupled to the processing unit and configured to receive configuration data from a remote location and to store the received configuration data in the storage device for retransmission, wherein the data transmission component is programmed to transmit a query to a remote location, and further wherein the data reception component receives the configuration data from the remote location in response to the transmitted query when one or more electronics in the remote location transitions from an inactive state to an active state upon detection of the query from the data transmission component.

Figure 2:
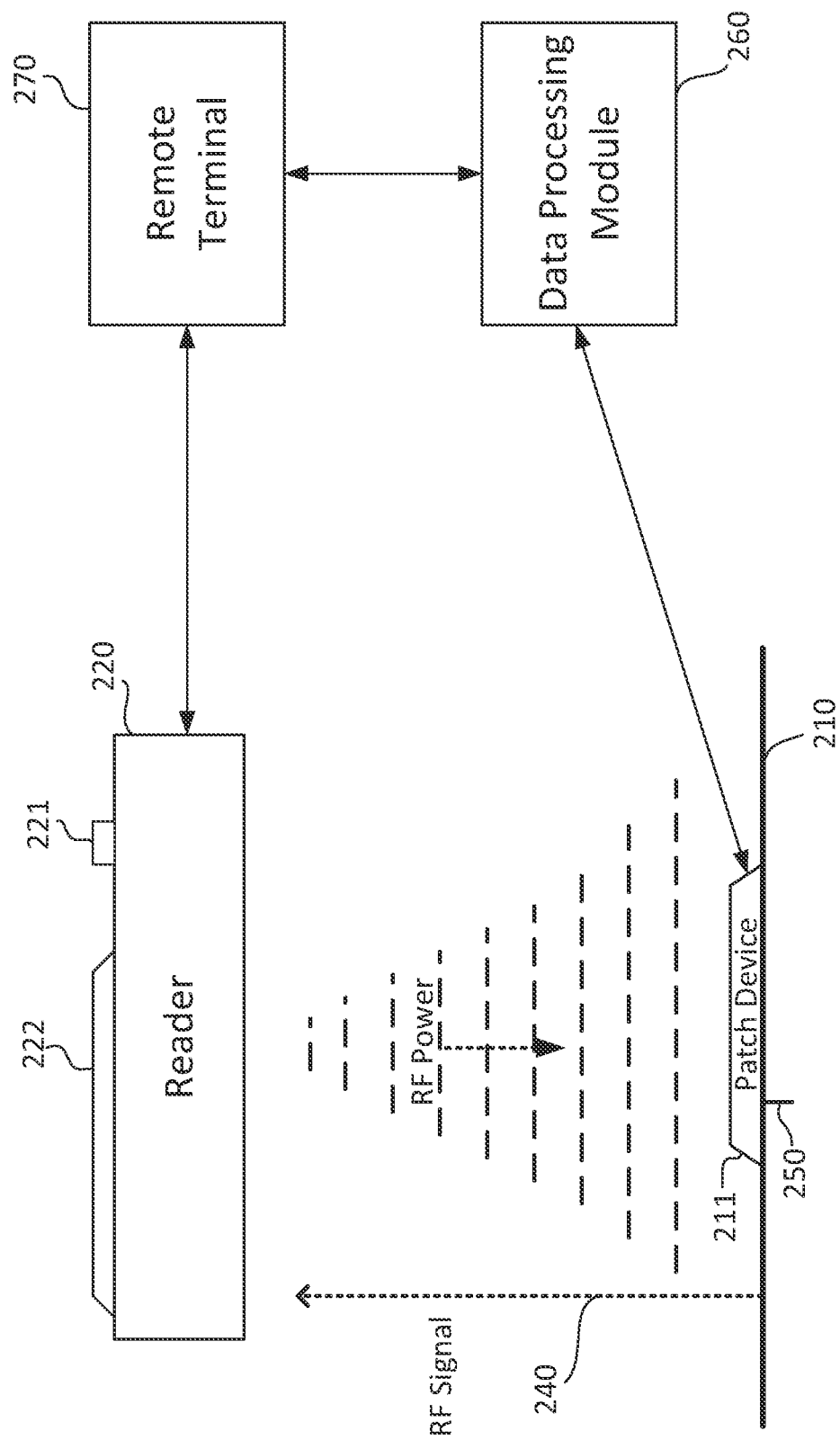
FIG. 2 illustrates a data monitoring and management system for real time glucose measurement data acquisition and processing in one aspect of the present disclosure.

FIG. 2 illustrates a data monitoring and management system for device configuration related data acquisition and processing in one aspect of the present disclosure. More specifically, as shown in FIG. 2, the on-body patch device 211 including sensor electronics coupled to an analyte sensor 250 is positioned on a skin surface 210 of a patient or a user.

Referring back to FIG. 2, as shown, when the reader device/receiver unit 220 is positioned or placed in close proximity and within a predetermined range of the on-body patch device 211, the RF power supply in the reader device/receiver unit 220 may be configured to provide the necessary power to operate the electronics in the on-body patch device 211, and the on-body patch device 211 may be configured to, upon detection of the RF power from the reader device/receiver unit 220, perform preprogrammed routines including, for example, transmitting one or more signals 240 to the reader device/receiver unit 220 indicative of the configuration of the analyte sensor 250.

In certain embodiments, the reader device/receiver unit 220 may include an RF power switch that is user activatable or activated upon positioning within a predetermined distance from the on-body patch device 211 to turn on the analyte sensor in the on-body patch device 211. That is, using the RF signal, the analyte sensor coupled to the sensor electronics in the on-body patch device 211 may be initialized or activated. In another embodiment, a passive RFID function may be provided or programmed such that upon receiving a "turn on" signal which, when authenticated, will turn on the electronic power switch that activates the on-body patch device 211. That is, the passive RFID configuration may include drawing energy from the RF field radiated from the reader device/receiver unit 220 so as to prompt for and/or detect the "turn on" signal which, upon authentication, activates the on-body patch device 211.

In one embodiment, communication and/or RF power transfer between the reader device/receiver unit 220 and the on-body patch device 211 may be automatically initiated when the reader device/receiver unit 220 is placed in close proximity to the on-body patch device 211 as discussed above. Alternatively, the reader device/receiver unit 220 may be configured such that user activation, such as data request initiation and subsequent confirmation by the user using, for example, the display 222 and/or input components 221 of the reader device/receiver unit 220, may be required prior to the initiation of communication and/or RF power transfer between the reader device/receiver unit 220 and the on-body patch device 211. In a further embodiment, the reader device/receiver unit 220 may be user configurable between multiple modes, such that the user may choose whether the communication between the reader device/receiver unit 220 and on-body patch device 211 is performed automatically or requires a user activation and/or confirmation.

As further shown in FIG. 2, the display 222 of the reader device/receiver unit 220 may be configured to provide the functionalities of a user interface to present information such as alarm or alert notification to the user. In one aspect, the reader device/receiver unit 220 may include other output components such as a speaker, vibratory output component and the like to provide audible and/or vibratory output indication to the user in addition to the visual output indication provided on the display 222.

As discussed, some or all of the electronics in the on-body patch device 211 in one embodiment may be configured to rely on the RF power received from the reader device/receiver unit 220 to perform transmission of the configuration information to the reader device/receiver unit 220. That is, the on-body patch device 211 may be discreetly worn on the body of the user or the patient, and under clothing, for example, and when desired, by positioning the reader device/receiver unit 220 within a predetermined distance from the on-body patch device 211, configuration information may be received by the reader device/receiver unit 220.

Referring still to FIG. 2, also shown are a data processing module/terminal 260 and a remote terminal 270. In one aspect, data processing module 260 may include a stand alone device configured for bi-directional communication to communicate with the on-body patch device 211, the reader device/receiver unit 220 and/or the remote terminal 270. More specifically, data processing module 260 may include one or more microprocessors or similar data processing components configured to execute one or more software routines for communication, as well as data storage and retrieval to and from one or more memory components provided in the housing of the data processing module 260.

The data processing module 260 in one embodiment may be configured to communicate with the on-body patch device 211 in a similar manner as the reader device/receiver unit 220 and may include communication components such as antenna, power supply and memory, among others, for example, to allow provision of RF power to the on-body patch device 211 or to request or prompt the on-body patch device 211 to send the configuration data and optionally stored analyte related data. The data processing module 260 may be configured to interact with the on-body patch device 211 in a similar manner as the reader device/receiver unit 220 such that the data processing module 260 may be positioned within a predetermined distance from the on-body patch device 211 for communication with the on-body patch device 211.

In one aspect, the on-body patch device 211 and the data processing module 260 may be positioned on the skin surface of the user or the patient within the predetermined distance of each other (for example, within approximately 5 inches or less) such that the communication between the on-body patch device 211 and the data processing module 260 is maintained. In a further aspect, the housing of the data processing module 260 may be configured to couple to or cooperate with the housing of the on-body patch device 211 such that the two devices are combined or integrated as a single assembly and positioned on the skin surface.

Referring again to FIG. 2, the data processing module 260 may be configured or programmed to prompt or ping the on-body patch device 211 at a predetermined time interval such as upon activation of the on-body patch device 211, or once every five minutes or once every 30 minutes or any other suitable or desired programmable time interval to request configuration data from the on-body patch device 211 which is received and is stored in one or more memory devices or components of the data processing module 260. In another embodiment, the data processing module 260 is configured to prompt or ping the on-body patch device 211 when desired by the patient or the user on-demand, and not based on a predetermined time interval.

As further shown in FIG. 2, the data processing module 260 in one aspect may be configured to transmit the stored data received from the on-body patch device 211 to the reader device/receiver unit 220 when communication between the data processing module 260 and the reader device/receiver unit 220 is established. More specifically, in addition to RF antenna and RF communication components described above, data processing module 260 may include components to communicate using one or more wireless communication protocols such as, for example, but not limited to, infrared (IR) protocol, Bluetooth protocol, Zigbee protocol, and 802.11 wireless LAN protocol. Additional description of communication protocols including those based on Bluetooth protocol and/or Zigbee protocol can be found in U.S. Patent Publication No. 2006/0193375 incorporated herein by reference for all purposes. The data processing module 260 may further include communication ports, drivers or connectors to establish wired communication with one or more of the reader device/receiver unit 220, on-body patch device 211, or the remote terminal 270 including, for example, but not limited to USB connector and/or USB port, Ethernet connector and/or port, FireWire connector and/or port, or RS-232 port and/or connector.

In one aspect, the data processing module 260 may be configured to operate as a data logger configured or programmed to periodically request or prompt the on-body patch device 211 to transmit the configuration information, and to store the received information for later retrieval or subsequent transmission to the reader device/receiver unit 220 or to the remote terminal 270 or both, for further processing and analysis.

In a further aspect, the functionalities of the data processing module 260 may be configured or incorporated into a memory device such as an SD card, microSD card, compact flash card, XD card, Memory Stick card, Memory Stick Duo card, or USB memory stick/device including software programming resident in such devices to execute upon connection to the respective one or more of the on-body patch device 211, the remote terminal 270 or the reader device/receiver unit 220. In a further aspect, the functionalities of the data processing module 260, including executable software and programming, may be provided to a communication device such as a mobile telephone including, for example, iPhone, iPod Touch, Blackberry device, Palm based device (such as Palm Pre, Treo, Treo Pro, Centro), personal digital assistants (PDAs) or any other communication enabled operating system (such as Windows or Android operating systems) based mobile telephones as a downloadable application for execution by the downloading communication device. To this end, the remote terminal 270 as shown in FIG. 2 may include a personal computer, or a server terminal that is configured to provide the executable application software to the one or more of the communication devices described above when communication between the remote terminal 270 and the devices are established.

Depending upon the user setting or configuration on the communication device, the downloaded application may be programmed or customized using the user interface of the respective communication device (screen, keypad, and the like) to establish or program the desired settings such as a receiver alarm, an insulin pump alarm, sensor replacement alarm, or any other alarm or alert conditions as may be desired by the user. Moreover, the programmed notification settings on the communication device may be output using the output components of the respective communication devices, such as speaker, vibratory output component, or visual output/display. As a further example, the communication device may be provided with programming and application software to communicate with the on-body patch device 211 such that a frequency or periodicity of data acquisition is established. In this manner, the communication device may be configured to conveniently receive configuration information from the on-body patch device 211 at predetermined time periods such as, for example, but not limited to during an activation of the on-body patch device 211, once every minute, once every five minutes, or once every 10 or 15 minutes, and store the received information, as well as to provide a desired or appropriate warning indication or notification to the user or the patient.

Figure 3:
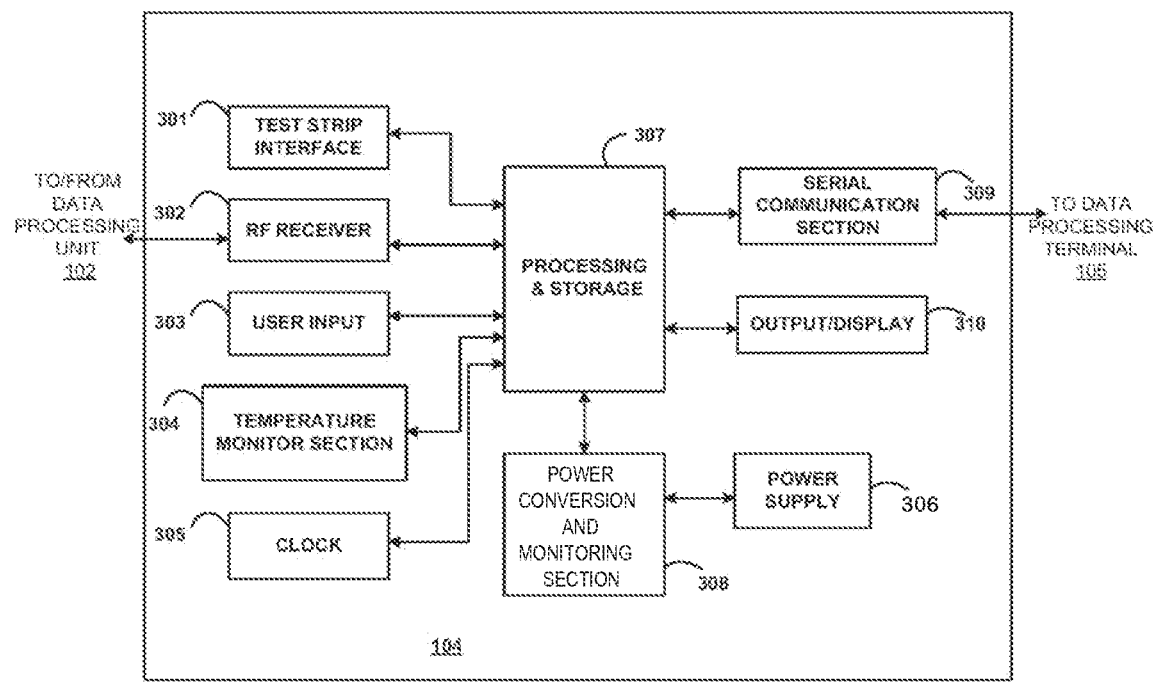
FIG. 3 is a block diagram of a receiver/monitor unit such as that shown in FIG. 1 in accordance with certain embodiments.

FIG. 3 is a block diagram of a receiver/monitor unit or insulin pump such as that shown in FIG. 1 in accordance with certain embodiments. The primary receiver unit 104 (FIG. 1) includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In one aspect, the RF receiver 302 is configured to communicate, via the communication link 103 (FIG. 1) with the data processing unit (sensor electronics) 102, to receive encoded data from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 may be configured to provide temperature information of the primary receiver unit 104 to the processing and control section 307, while the clock 305 provides, among others, real time or clock information to the processing and storage section 307.

Each of the various components of the primary receiver unit 104 shown in FIG. 3 is powered by the power supply 306 (or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. The serial communication section 309 in the primary receiver unit 104 is configured to provide a bi-directional communication path from the testing and/or manufacturing equipment for, among others, initialization, testing, and configuration determination of the primary receiver unit 104.

Serial communication section 104 can also be used to upload data to a computer, such as configuration data. The communication link with an external device (not shown) can be made, for example, by cable (such as USB or serial cable), infrared (IR) or RF link. The output/display 310 of the primary receiver unit 104 is configured to provide, among others, a graphical user interface (GUI), and may include a liquid crystal display (LCD) for displaying information. Additionally, the output/display 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processor 307, or provided separately in the primary receiver unit 104, operatively coupled to the processor 307. The processor 307 may be configured to perform Manchester decoding (or other protocol(s)) as well as error detection and correction upon the encoded data received from the data processing unit 102 via the communication link 103.

In further embodiments, the data processing unit 102 and/or the primary receiver unit 104 and/or the secondary receiver unit 106, and/or the data processing terminal/infusion section 105 of FIG. 1 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions are provided in U.S. Pat. Nos. 5,262,035; 5,264,104; 5,320,715; 5,593,852; 6,175,752; 6,650,471; 6,746,582, 6,284,478, 7,299,082, and 7,811,231, in application Ser. No. 11/060,365, filed Feb. 16, 2005 titled "Method and System for Providing Data Communication in Continuous Glucose Monitoring And Management System", in application Ser. No. 12/698,124, filed Feb. 1, 2010, titled "Compact On-Body Physiological Monitoring Devices and Methods Thereof", and in application Ser. No. 12/807,278, filed Aug. 31, 2010 titled "Medical Devices and Methods", each of which is incorporated herein by reference.

Sensors for continuous glucose monitoring systems can be continually improved and these updated versions of the sensors will be made available to consumers. An important consideration for updated sensor products is to ensure that on market system components (e.g., receiver devices, repeater units, glucose meters, insulin pumps, etc.) will work with specific components of the sensor that has been updated. Another consideration is to exclude updated components from operation with certain components if such operation is not safe and effective. For instance, some CGM algorithms may be designed to work with a particular type of sensor but not with others.

In certain embodiments, electronic system update configuration requirements can be enforced using key codes that are incorporated in the communication messages sent between system components. Sensor configuration updates can be managed using a key code technique. Since sensors themselves may not be capable of interacting with other components using key codes, such features may be integrated along with the sensor or sensor delivery system. For instance, in some embodiments, the sensor may provide a radio ID or a resistive code to indicate its configuration to the other system components. The sensor electronics (e.g., transmitter) may use these means to detect the sensor version in order to further manage component configuration (e.g., communicating the sensor version information to other components using key codes). The sensor electronics may have a range of sensor codes that it can accept, or the sensor electronics may pass the sensor code data to the receiver device (or other device in the system) that can have a range of sensor codes that it accepts. Similarly, the transmitter can have a range of acceptable receiver codes and a receiver can have a range of acceptable transmitter codes. In certain embodiments, if the receiver device detects a sensor version that is not allowable or if the transmitter sends the receiver a message indicating that the attached sensor was not allowable, it can notify the user that the sensor version is not allowable. Moreover, the transmitter and/or receiver software can change algorithms or other software functions dependent on the detected software version.

In certain embodiments, key codes can be incorporated in communication messages sent through the devices in the analyte monitoring system. Key codes are primarily available for access by electronic devices. The codes may be used as a book keeping tool to manage which version of the device may function with specific versions of a device application using a particular serial command. For example, a serial command may include a two byte key code that can be issued by a value of code=00 when it sends the command to a device. An original version of a device can be designed with a serial command function that will accept commands with a code range of 00 to 0F, for example. In this manner, if another version of the device has an updated serial command that allows a code range, e.g., of 00 to 1F, then the original device application can still work with the original device, as well as any newer version of the device application that has codes in this range (e.g., specifically to a particular serial command). If an updated devices application is not intended to be compatible with the original device version but only a new device version, then the code for the device application could be set between 10 to 1F. If the updated device is not intended to work with the original device application, then the code for the device can be set to 10 to 1F.

In certain embodiments, the key code mechanism includes a key code communicated in a pairing message exchange between two devices in the analyte monitoring system, in the same manner as described above for device serial commands accessed by a device application. In this case, the key code only needs to be included in a pairing message in order to enforce all communication restrictions between version of the device and the analyte monitoring system, since they may not communicate (e.g., except for pairing attempts) unless they are paired. This aspect can allow for full control over which device versions will work with the analyte monitoring system.

By way of example, in some embodiments, a device could be designed to accept serial commands with names $acona, $aconb, and $aconx, and the device application can issue $aconb. Moreover, the device could be designed to accept a serial command with three parameters and with five parameters.

In other embodiments, a configuration management mechanism is arranged to mechanically key the sensor to only function with a particular transmitter. For example, the sensor electrode contacts may be located in ways to allow some transmitters to properly connect and others to not. Additionally, the sensor can be incorporated into a transmitter mount that mechanically only fits the desired transmitter.

Certain embodiments allow interoperability of various sensor versions with common transmitters and receivers but enforce compatibility requirements at the receiver or other device in the system by requiring that a sensor code be entered prior to glucose calculation and display. The sensor code can be used to define a range of acceptable sensitivity of the device, and may be used to specify the sensitivity itself or contribute to the glucose calculation. Moreover, the sensor may have additional elements that identify the sensor version. Likewise, the sensor code may be used exclusively to identify the sensor version. Then the receiver device can compare the entered sensor code to a list of acceptable codes and if successful, allow glucose calculations or display. Otherwise, the receiver can notify the user that the sensor is not compatible. Furthermore, the receiver software can change algorithms or other software function dependent upon the entered sensor code.

Figure 4:
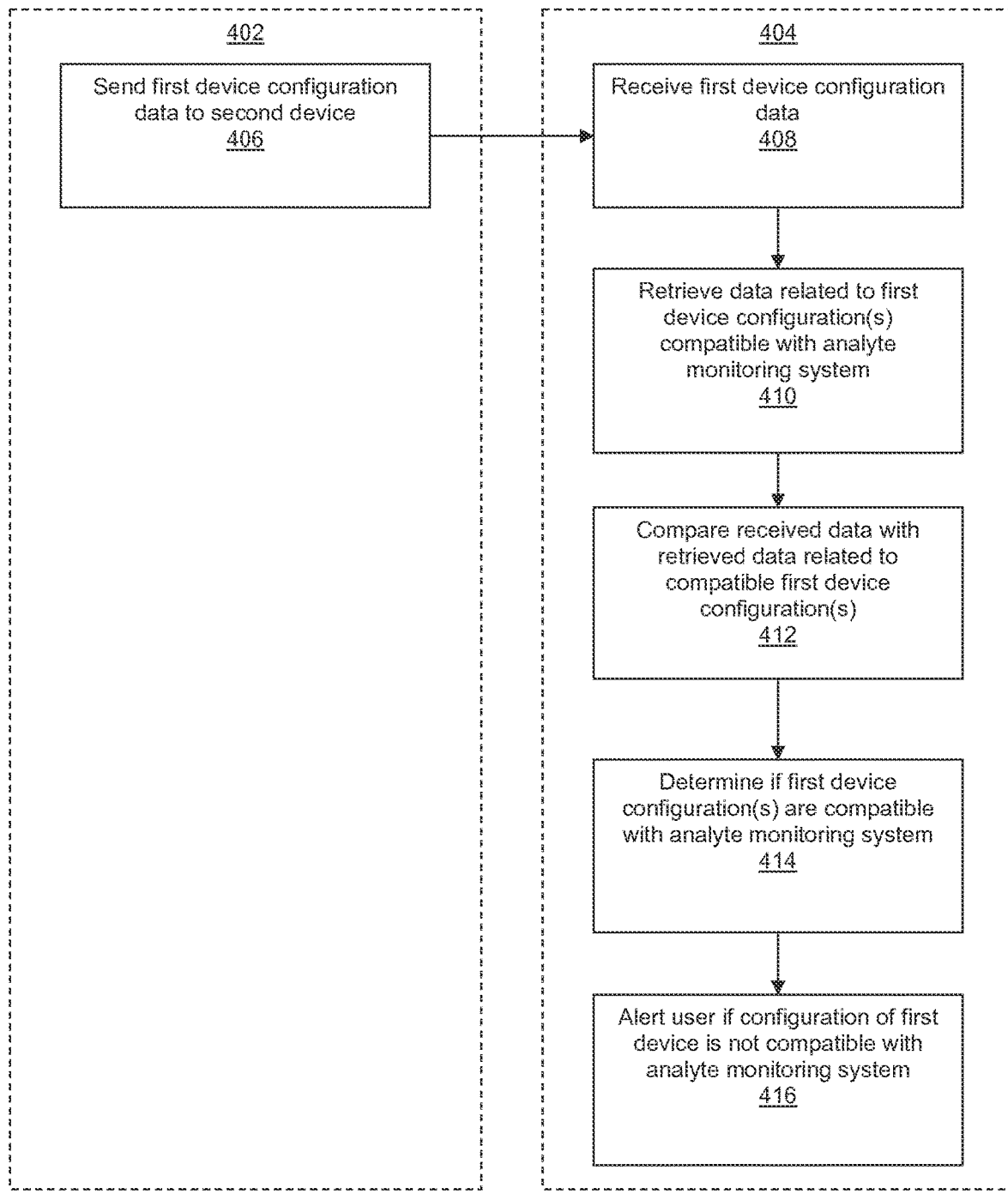
FIG. 4 is a flowchart illustrating a method for determining a compatibility of one or more devices in an analyte monitoring system in accordance with certain embodiments of the present disclosure.

FIG. 4 is a flow diagram illustrating steps in an embodiment for determining the compatibility of a first device 402 in an analyte monitoring system 400. The first device 402 and the second device 404 in the analyte monitoring system 400 can each include at least one of a receiver device, an analyte meter, a glucose monitor, an insulin pump, a continuous analyte monitor, a cellular phone, a personal digital assistant, a personal computer, a laptop computer, and/or a repeater unit. In certain embodiments, a first device 402 sends data related to its configuration to the second device 404 (406). The request can be sent, for example, wirelessly from the transmitter of the first device 402 to the transceiver of the second device 404. The configuration of first device 402, which can be an analyte sensor, can embody one or more various configurations that include different versions of the analyte sensor. Each of the configurations of the first device 402 can include various specifications associated therewith, such as a specific calibration factor and a software function that is used to process analyte data that is obtained by the first device 402. The analyte data can be processed using the software function at the first device 402 or one or more different devices.

Referring still to FIG. 4, the second device 404 receives the data related to the configuration of the first device 402 (408). The second device 404 then retrieves data that is related to configurations that are compatible with the analyte monitoring system 400 (410). The data related to the compatible configurations can be retrieved by the second device 404, for example, from one or more of at least one storage component of the second device 402, an internet based server, from a central server, and/or a distributed server. Next, the second device 404 compares the received data related to the configuration of the first device 402 with the retrieved data that is related to one or more configurations that are compatible with the analyte monitoring system 400 (412). The second device 404 determines if the configuration of the first device 402 is compatible with the analyte monitoring system 400, based upon the comparison of the received data related to the configuration of the first device 402 with the retrieved data related to one or more configurations compatible with analyte monitoring system 400 (414). The second device 404 annunciates or otherwise communicates an alarm to alert a user if it is determined that the first device 402 is not compatible with the analyte monitoring system 400 (416). The alarm may be at least one of an audio alarm, a vibratory alarm, and a visual alarm operatively coupled to the second device 404. If however, the first device 402 is determined to be compatible with the analyte monitoring system 400, then the first device 402 may proceed to obtain analyte data from the user.

Figure 5:
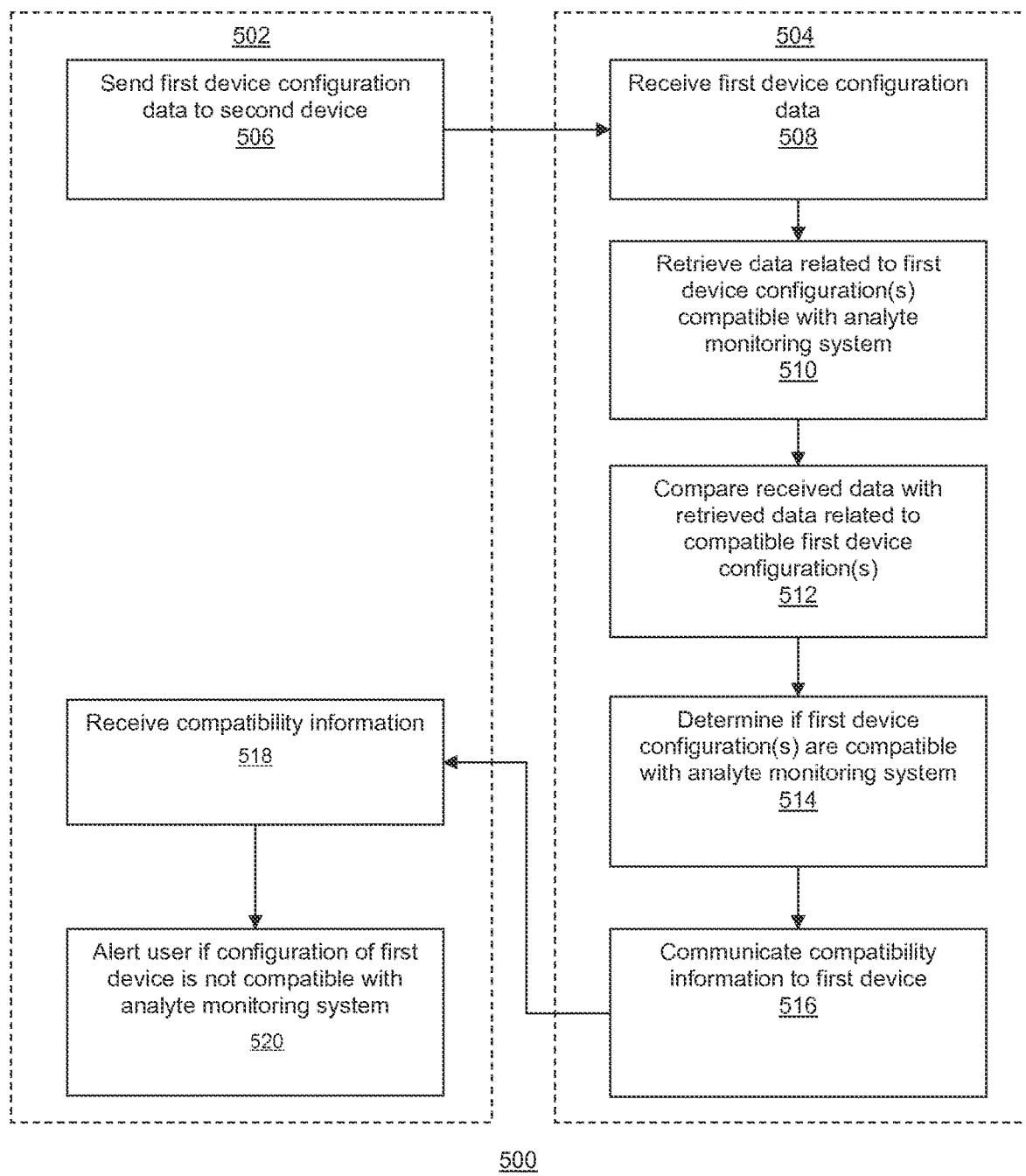
FIG. 5 is a flowchart illustrating a method for determining a compatibility of one or more devices in an analyte monitoring system in accordance with certain embodiments of the present disclosure.

FIG. 5 is a flow diagram illustrating steps in an embodiment for determining the compatibility of a first device 502 in an analyte monitoring system 500. The first device 502 and the second device 504 in the analyte monitoring system 500 can each include at least one of a receiver device, an analyte meter, a glucose monitor, an insulin pump, a continuous analyte monitor, a cellular phone, a personal digital assistant, a personal computer, a laptop computer, and/or a repeater unit. In certain embodiments, a first device 502 sends data related to its configuration to the second device 504 (506). The request can be sent, for example, wirelessly from the transmitter of the first device 502 to the transceiver of the second device 504. The configuration of first device 502, which can be an analyte sensor, can embody one or more various configurations that include different versions of the analyte sensor. Each of the configurations of the first device 502 can include various specifications associated therewith, such as a specific calibration factor and a software function that is used to process analyte data that is obtained by the first device 502. The analyte data can be processed using the software function at the first device 502 or one or more different devices.

Referring still to FIG. 5, the second device 504 receives the data related to the configuration of the first device 502 (508). The second device 504 then retrieves data that is related to the configurations the first device 502 may embody that are compatible with the analyte monitoring system 500 (510). The data related to the compatible configurations can be retrieved by the second device 504, for example, from one or more of at least one storage component of the second device 502, an internet based server, from a central server, and/or a distributed server. Next, the second device 504 compares the received data related to the configuration of the first device 502 with the retrieved data that is related to one or more configurations that are compatible with the analyte monitoring system 500 (512). The second device 504 determines if the configuration of the first device 502 is compatible with the analyte monitoring system 500, based upon the comparison of the received data related to the configuration of the first device 502 with the retrieved data related to one or more configurations compatible with analyte monitoring system 500 (514). Following the compatibility determination, the second device 504 communicates, to the first device 502, data related to the compatibility determination to the first device 502 (516). The data can be communicated, for example, from a transmitter of the second device 504 to a transceiver of the first device 502.

Still referring to FIG. 5, the first device 502 receives the data related to its compatibility with the analyte monitoring system 500 from the second device 504 (518) and alerts a user if it was determined by the second device 504 that the first device 502 is not compatible with the analyte monitoring system 500 (520), by annunciating or otherwise communicating an alarm. The alarm may be at least one of an audio alarm, a vibratory alarm, and a visual alarm. If the first device 502 is determined to be compatible with the analyte monitoring system 500, then the first device 502 may proceed to obtain analyte data from the user.

In another embodiment, the compatibility data can be transmitted to and subsequently received by a third device (not shown), and the third device can annunciate or otherwise communicate an alarm to alert the user if the first device 502 is determined to not be compatible with the analyte monitoring system 500.

Figure 6:
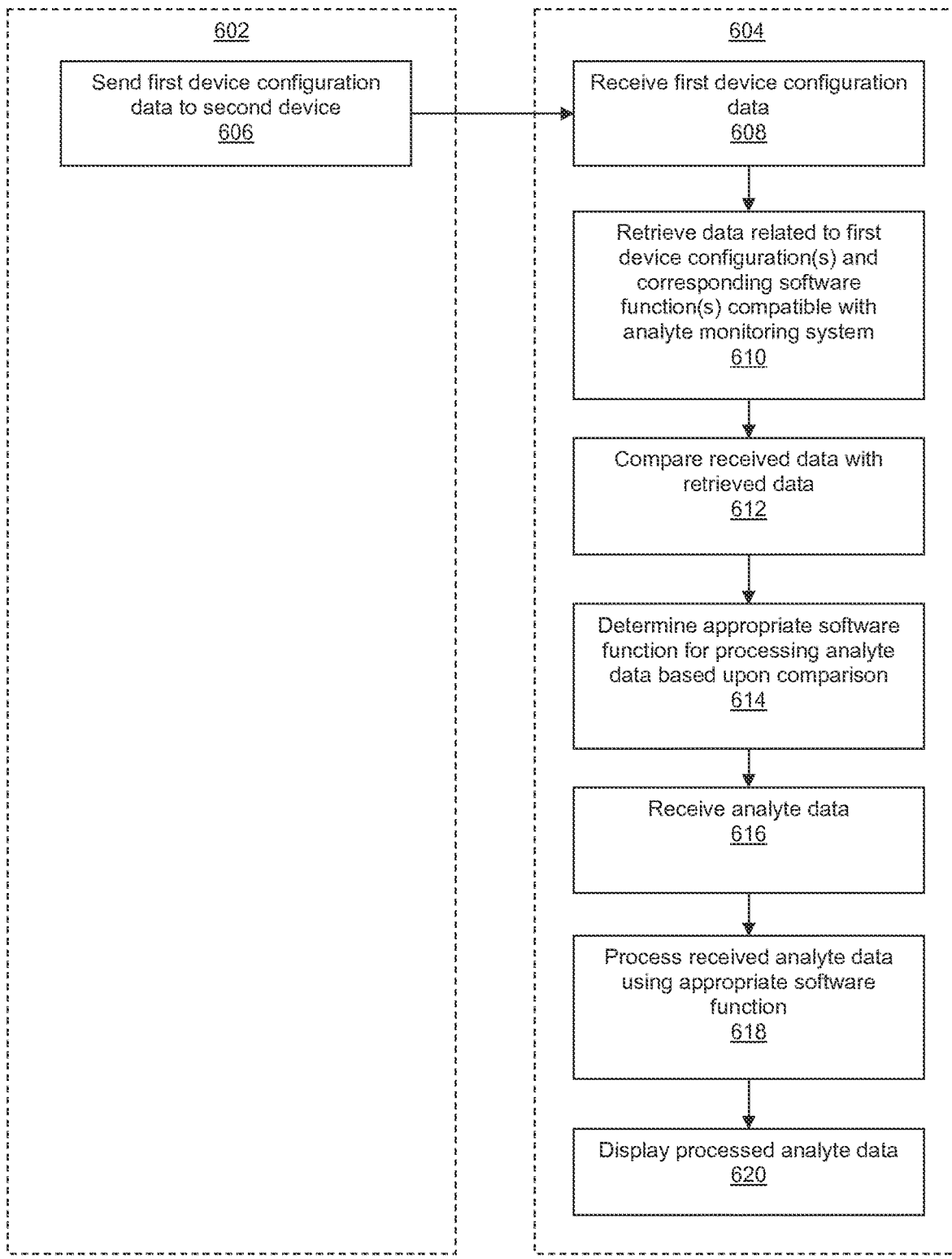
FIG. 6 is a flowchart illustrating a method for determining a compatibility of one or more devices in an analyte monitoring system in accordance with certain embodiments of the present disclosure.

FIG. 6 is a flow diagram illustrating steps in an embodiment for determining the compatibility of a first device 602 in an analyte monitoring system 600. The first device 602 and the second device 604 in the analyte monitoring system 600 can each include at least one of a receiver device, an analyte meter, a glucose monitor, an insulin pump, a continuous analyte monitor, a cellular phone, a personal digital assistant, a personal computer, a laptop computer, and/or a repeater unit. In certain embodiments, the first device 602 sends data related to its configuration to a second device 604 (606). The data can be sent, for example wirelessly from the transmitter of the first device 602 to the transceiver of the second device 604. The configuration of first device 602, which can be an analyte sensor, can embody one or more various configurations that include different versions of the analyte sensor. Each of the configurations of the first device 602 can include various specifications associated therewith, such as a specific calibration factor and a software function that is used to process analyte data that is obtained by the first device 602. The analyte data can be processed using the software function at the first device 602 or one or more different devices.

Referring still to FIG. 6, the second device 604 receives the data related to the configuration of the first device 602 (608). The second device 604 then retrieves data that is related to one or more compatible configurations of the first device 604 (610). In certain embodiments, the data includes software functions that correlate to the one or more compatible configurations of the first device. The data can be retrieved, for example, from one or more storage components of the second device 602, an internet based server, from a central server, and/or a distributed server. Moreover, the data related to the one or more compatible configurations of the first device 602, and the software functions correlated to the one or more compatible configurations can be stored at the same or separate locations, and can be retrieved at the same time as the compatibility data or at a different time. The second device 604 compares the received data with the retrieved data (612) and determines an appropriate software function that is correlated with the configuration of the first device 602 (614). The software function can be used to process analyte data that is received from the first device 602. The second device 604 receives analyte data that is obtained from the first device 602 (616), which can be sent, for example, wirelessly from the transmitter of the first device 602 to the transceiver of the second device 604. The second device 604 then processes the received analyte data using the determined appropriate software function (618) and displays the processed analyte data to a user (620).

In another embodiment, the second device 604 can communicate data related to the software function associated with the configuration of the first device 602 to a third device (not shown). The analyte data can be communicated from the first device 602 to the third device, and the third device can process the analyte data using the data related to the software function received from the second device 604. The third device may also display the processed analyte data to the user.

In certain embodiments of the present disclosure, a computer-implemented method for determining a compatibility of one or more devices in an analyte monitoring system includes receiving identification code data related to a configuration of a first device, retrieving information including a predetermined list of one or more acceptable identification code data that is related to one or more first device configurations that are compatible with the analyte monitoring system, comparing the received identification code data with the one or more acceptable identification codes from the retrieved predetermined list, and determining if the configuration of the first device is compatible with the analyte monitoring system, based upon the received identification code data being identified in the predetermined list of acceptable identification code data.

Certain aspects include alerting a user if it is determined that the configuration of the first device is not compatible with the analyte monitoring system.

Certain aspects include communicating data related to the determination of the first device being compatible with the analyte monitoring system of a second device.

Certain aspects include the first device communicating the data related to the compatibility of the first device to the second device using at least one key code.

Certain aspects include the data related to the compatibility to the first device communicated using at least one of a radio-identification code or a resistive code or a combination thereof.

Certain aspects include the identification code data including information related to a range of acceptable sensitivity of the first device.

Certain aspects include the identification code data including information related to a version of the first device.

Certain aspects include the user being alerted with at least one of an auditory alarm, a vibratory alarm, and a visual alarm.

Certain aspects include the first device being in fluid contact with an interstitial fluid under a skin layer of a user.

Certain aspects include determining a suitable software function for processing analyte data obtained by the first device, based upon a stored software function that corresponds to the received identification code data, wherein the software function is included in the information related to a predetermined list of one or more acceptable identification code data.

Certain aspects include receiving analyte data obtained by the first device that is related to an analyte level of a user, if it is determined that the first device is compatible with the analyte monitoring system, processing the received analyte data using the determined appropriate software function, and displaying the processed analyte data to the user.

Certain aspects include the compatibility of the first device including a key code of the first device being included in the predetermined list.

Certain aspects include the first device including at least one of a continuous analyte monitor, an analyte sensor, a receiver device, a repeater device, or an insulin pump.

In certain embodiments of the present disclosure, a computer-implemented method for determining a compatibility of one or more devices in an analyte monitoring system includes receiving identification code data related to a configuration of a first device, retrieving information including a predetermined list of one or more identification codes that are related to one or more first device configurations and one or more software functions relating to the one or more first device configurations, comparing the received identification code data with the one or more identification codes, and determining an appropriate software function for processing analyte data obtained by the first device that is related to an analyte level of a user, based upon a stored software function that corresponds to the received identification code data.

Certain aspects include the software function including an algorithm.

Certain aspects include the first device including at least one of a continuous analyte monitor, an analyte sensor, a receiver device, a repeater device, or an insulin pump.

Certain aspects include the information including the predetermined list and the one or more software functions retrieved from at least one of a storage component, an online database, a central database, and a distributed database.

Certain aspects include the information including the predetermined list and the one or more software functions retrieved from different locations.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A method, comprising the steps of:
   determining, by one or more processors of a reader device, whether a drug delivery device is compatible with a reader device based at least on data related to a configuration of the drug delivery device received by the reader device;
   determining, by the one or more processors of the reader device, whether an integrated sensor and sensor electronics assembly are compatible with the reader device based at least on data related to a configuration of the integrated sensor and sensor electronics assembly received by the reader device;
   processing, by the one or more processors of the reader device, data indicative of an analyte level of a user received from the integrated sensor and sensor electronics assembly in response to a determination that the integrated sensor and sensor electronics assembly are compatible with the reader device; and
   displaying the processed data indicative of the analyte level of the user on the reader device.

2. The method of claim 1, wherein the data related to the configuration of the integrated sensor and sensor electronics assembly comprises an identification code.

3. The method of claim 1, wherein the data related to the configuration of the integrated sensor and sensor electronics assembly comprises a key code.

4. The method of claim 1, further comprising the step of communicating a first alarm to the user in response to a determination that the integrated sensor and sensor electronics assembly is not compatible.

5. The method of claim 4, wherein the first alarm comprises at least one of an audio alarm, a vibratory alarm, and a visual alarm.

6. The method of claim 1, further comprising the step of communicating a second alarm to the user in response to a determination that the drug delivery device is not compatible.

7. The method of claim 6, wherein the second alarm comprises at least one of an audio alarm, a vibratory alarm, and a visual alarm.

8. The method of claim 1, wherein the drug delivery device is an insulin pump.

9. The method of claim 1, wherein determining, by one or more processors of a reader device, whether the integrated sensor and sensor electronics assembly are compatible with the reader device comprises comparing a sensor version of the integrated sensor and sensor electronics assembly with a predetermined list.

10. The method of claim 9, further comprising the step of selecting a software function based on the sensor version of the integrated sensor and sensor electronics assembly.

11. The method of claim 1, further comprising the step of:
   receiving, by a watch, the data indicative of the analyte level of the user from the sensor electronics assembly or from the reader device.

12. A method, comprising the steps of:
   determining, by one or more processors of a reader device, whether an integrated sensor and sensor electronics assembly are compatible with the reader device based at least in part on an identification code related to a configuration of the integrated sensor and sensor electronics assembly received by the reader device;
   processing, by one or more processors of a reader device, data indicative of an analyte level of a user received from the integrated sensor and sensor electronics assembly using a software function correlated with the configuration of the integrated sensor and sensor electronics assembly; and
   displaying the processed data indicative of the analyte level of the user on the reader device.

13. The method of claim 12, further comprising the step of determining, by one or more processors of a reader device, whether a drug delivery device is compatible with a reader device based at least on data related to a configuration of the drug delivery device received by the reader device.

14. The method of claim 12, further comprising the step of communicating a first alarm to the user in response to a determination that the integrated sensor and sensor electronics assembly is not compatible.

15. The method of claim 12, further comprising the step of:
   receiving, by a watch, the data indicative of the analyte level of the user from the sensor electronics assembly or from the reader device.

16. A method, comprising the steps of:
   determining, by one or more processors of a reader device, whether a drug delivery device is compatible with a reader device based at least on data related to a configuration of the drug delivery device received by the reader device;
   determining, by the one or more processors of the reader device, whether an integrated sensor and sensor electronics assembly are compatible with the reader device based at least on data related to a configuration of the integrated sensor and sensor electronics assembly received by the reader device;
   receiving, by a receiver of the drug delivery device, data indicative of the analyte level of the user; and displaying, one or more processors of the drug delivery device, processed data indicative of the analyte level of the user.

17. The method of claim 16, further comprising the steps of:
   determining, by the one or more processors of the reader device, whether an integrated sensor and sensor electronics assembly are compatible with the reader device based at least on data related to a configuration of the integrated sensor and sensor electronics assembly received by the reader device;
   processing, by the one or more processors of the reader device, data indicative of an analyte level of a user received from the integrated sensor and sensor electronics assembly in response to a determination that the integrated sensor and sensor electronics assembly are compatible with the reader device; and
   displaying the processed data indicative of the analyte level of the user on the reader device.

18. The method of claim 16, further comprising the step of:
   receiving, by the receiver of the drug delivery device, a software function correlated with a configuration of the integrated sensor and sensor electronics assembly.

19. The method of claim 18, further comprising the step of:
   processing the data indicative of the analyte level of the user using the software function correlated with the configuration of the integrated sensor and sensor electronics assembly from the reader device.

20. The method of claim 18, wherein the software function is retrieved from a server.

21. The method of claim 18, wherein the software function is retrieved from one or more components of the reader device.

22. The method of claim 16, further comprising the step of:
   receiving, by a watch, the data indicative of the analyte level of the user from the sensor electronics assembly or from the reader device.

* * * * *